(12) United States Patent
Mihan et al.

(10) Patent No.: US 6,787,498 B2
(45) Date of Patent: Sep. 7, 2004

(54) MONOCYCLOPENTADIENYL COMPLEXES OF CHROMIUM, MOLYBDENUM OR TUNGSTEN

(75) Inventors: Shahram Mihan, Ludwigshafen (DE); Dieter Lilge, Limburgerhof (DE); Paulus de Lange, Limburgerhof (DE); Günther Schweier, Friedelsheim (DE); Martin Schneider, Ludwigshafen (DE); Ursula Rief, Heddesheim (DE); Udo Handrich, Hassloch (DE); Johannes Hack, Grünstadt (DE); Markus Enders, Heidelberg (DE); Gunter Ludwig, Steinsfurt (DE); Ralph Rudolph, Mannheim (DE)

(73) Assignee: Basell Polyolefine GmbH, Wesseling (DE)

( * ) Notice: Subject to any disclaimer, the term of this patent is extended or adjusted under 35 U.S.C. 154(b) by 0 days.

(21) Appl. No.: 10/166,140

(22) Filed: Jun. 11, 2002

(65) Prior Publication Data

US 2003/0036662 A1 Feb. 20, 2003

Related U.S. Application Data

(62) Division of application No. 09/373,715, filed on Aug. 13, 1999, now Pat. No. 6,437,161.

(51) Int. Cl.$^7$ .......................... B01J 31/00; C07F 17/00; C07F 11/00; C08F 4/44
(52) U.S. Cl. .......................... 502/120; 556/11; 556/12; 556/21; 556/60; 546/10; 526/127; 526/160; 526/352; 526/943; 502/102; 502/117; 502/159
(58) Field of Search ................ 556/11, 12, 21, 556/60; 546/10; 502/102, 117, 120, 159; 526/127, 160, 352, 943

(56) References Cited

U.S. PATENT DOCUMENTS 3,709,853 A    1/1973   Karapinka ................... 260/88
4,015,059 A    3/1977   Karol ......................... 526/130
5,808,122 A    9/1998   Herrmann et al. ............. 556/58

FOREIGN PATENT DOCUMENTS

| DE | 19630580 | 2/1998 |
| DE | 19710615 | 9/1998 |
| WO | WO 96/13529 | 5/1996 |
| WO | WO 01/12687 | 2/2001 |
| WO | WO 01/92346 | 12/2001 |

OTHER PUBLICATIONS

Araki et al., Chemical Abstracts, vol. 119, No. 15, p. 957, abstract No. 160483p (1993).

Liang et al., Organometallics, vol. 15, pp. 5284–8286 (1996).

Jutzi et al., J. Org. Chem., vol. 500, pp. 175–185 (1995).

Enders et al., Chem. Ber., vol. 129, pp. 459–463 (1996).

Blais et al., Organometallics, vol. 17, pp. 3775–3783 (1998).

Enders et al., J. Org. Chem., vol. 549, pp. 251–256 (1997).

Enders et al., Book of Abstracts, Part 1, D091 (18$^{th}$ Int. Conf. on Organomet. Chemistry, Munich, Aug. 16–21, 1998).

Mise et al., Preparation and structure of the first ansa–molybdenocene and tungstenocene derivatives . . . , J. Organomet. Chem. 473, 155–162 (1994).

Döhring et al., Donor–Ligand–Substituted Cyclopentadienylchromium(III) Complexes: A New Class of Alkene Polymerization Catalysts . . . , Organometallics 4, 388–402 (2000).

*Primary Examiner*—Porfirio Nazario-Gonzalez
(74) *Attorney, Agent, or Firm*—Kell & Weinkauf

(57) ABSTRACT

Substituted monocyclopentadienyl, monoindenyl, monofluorenyl and heterocyclopentadienyl complexes of chromium, molybdenum or tungsten in which at least one of the substituents on the cyclopentadienyl ring carries a donor function which is bonded rigidly, not exclusively via sp$^3$-hybridized carbon or silicon atoms, and a process for the polymerization of olefins.

17 Claims, No Drawings

MONOCYCLOPENTADIENYL COMPLEXES OF CHROMIUM, MOLYBDENUM OR TUNGSTEN

This application is a divisional of prior application Ser. No. 09/373,715, filed Aug. 13, 1999, now U.S. Pat. No. 6,437,161.

The present invention relates to substituted monocyclopentadienyl, monoindenyl, monofluorenyl and heterocyclopentadienyl complexes of chromium, molybdenum or tungsten in which at least one of the substituents on the cyclopentadienyl ring carries a donor function which is bonded rigidly, not exclusively via sp$^3$-hybridized carbon or silicon atoms, and to a process for the polymerization of olefins.

Many of the catalysts used for the polymerization of α-olefins are based on immobilized chromium oxides (see, for example, Kirk-Othmer, "Encyclopedia of Chemical Technology", 1981, Vol.16, p. 402). These generally give ethylene hompolymers and copolymers of high molecular weights, but are relatively insensitive to hydrogen and thus do not allow simple control of the molecular weight. By contrast, use of bis(cyclopentadienyl)chromium (U.S. Pat. No. 3,709,853), bis(indenyl)chromium or bis(fluorenyl) chromium (U.S. Pat. No. 4,015,059) applied to an inorganic, oxidic support allows simple control of the molecular weight of polyethylene by addition of hydrogen.

As in Ziegler-Natta systems, there has recently also been interest in finding chromium catalyst systems having a uniformly defined active center, so-called single-site catalysts. By targeted variation of the ligand structure, the aim is to be able to modify in a simple manner the activity and copolymerization behavior of the catalyst and the properties of the resultant polymers.

Thus, EP-A-742046 discloses so-called constrained geometry complexes of the group 6, a special process for their preparation (via metal tetraamides), and a process for the preparation of a polyolefin in the presence of such catalysts. The ligand structure consists of an anionic donor which is linked to a cyclopentadienyl radical.

K. H. Theopold et al. in Organomet. 1996, 15, 5284–5286, have described an analogous {[(tert-butylamido)dimethylsilyl](tetramethylcyclopentadienyl)} chromium chloride complex for the polymerization of olefins. This complex selectively polymerizes ethylene. It is not possible either to incorporate comonomers, for example hexene, nor to polymerize propene.

This disadvantage can be overcome by using structurally very similar systems. For example, DE-A1-19710615 describes monocyclopentadienylchromium compounds substituted by donor ligands which can be used, for example, to polymerize propene as well. The donor in these compounds is from the 15th group of the Periodic Table of the Elements and is neutral. The donor is bonded to the cyclopentadienyl ring via a $(ZR_2)_n$ fragment, where R is hydrogen, alkyl or aryl, Z is an atom from the 14th group of the Periodic Table of the Elements, and n is 1. DE-A1-19630580 states that the combination of Z=carbon with an amine donor gives good results.

WO-A-96/13529 describes reduced transition-metal complexes from Groups 4 to 6 of the Periodic Table of the Elements with polydentate monoanionic ligands. These include, inter alia, cyclopentadienyl ligands, preferably containing a donor function bonded via a $(CR_2)_p$ bridge, where R is hydrogen or a hydrocarbyl radical having 1 to 20 carbon atoms, and p is 1 to 4. The preferred transition metal is titanium.

There are also ligand systems in which the donor group is linked rigidly to the cyclopentadienyl radical. Such ligand systems and their metal complexes are reviewed, for example, by P. Jutzi and U. Siemeling in J. Organomet. Chem. (1995), 500, 175–185, Section 3. M. Enders et. al., in Chem. Ber. (1996), 129, 459–463, describe 8-quinolyl-substituted cyclopentadienyl ligands and their titanium and zirconium trichloride complexes. 2-Picolylcyclopentadienyltitanium trichloride in combination with methylaluminoxane has been used by M. Blais, J. Chien and M. Rausch in Organomet. (1998), 17 (17) 3775–3783 for the polymerization of olefins.

It is an object of the present invention to find novel catalyst systems which can easily be modified and are suitable for the polymerization of α-olefins.

We have found that this object is achieved by substituted monocyclopentadienyl, monoindenyl, monofluorenyl and heterocyclopentadienyl complexes of chromium, molybdenum or tungsten in which at least one of the substituents on the cyclopentadienyl ring carries a donor function which is bonded rigidly, not exclusively via sp$^3$-hybridized carbon or silicon atoms.

We have furthermore found a process for the polymerization or copolymerization of olefins in which olefins are polymerized in the presence of the following components:

(A) a substituted monocyclopentadienyl, monoindenyl, monofluorenyl or heterocyclopentadienyl complex as claimed in claim 1, of the formula I

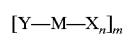         I, where:

M is chromium, molybdenum or tungsten

Y is described by the formula II

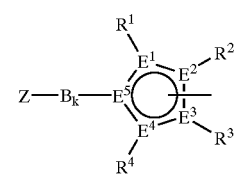

where:

$E^1$–$E^5$ are carbon or a maximum of one $E^1$ to $E^5$ is phosphorus or nitrogen, Z is $NR^5R^6$, $PR^5R^6$, $OR^5$, $SR^5$ or an unsubstituted, substituted or fused, partially unsaturated heterocyclic or heteroaromatic ring system, B is one of the following groups:

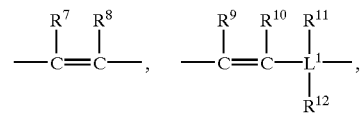

and in addition, if Z is an unsubstituted, substituted or fused, partially unsaturated heterocyclic or heteroaromatic ring system, may alternatively be

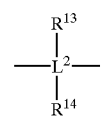

where $L^1$ and $L^2$ are silicon or carbon, k is 1, and is alternatively 0 if Z is an unsubstituted, substituted or fused, partially unsaturated heterocyclic or heteroaromatic ring system, X independently of one another, are fluorine, chlorine, bromine, iodine, hydrogen, $C_1$–$C_{10}$-alkyl, $C_2$–$C_{10}$-alkenyl, $C_6$–$C_{20}$-aryl, alkylaryl having 1–10 carbon atoms in the alkyl radical and 6–20 carbon atoms in the aryl radical, $NR^{15}R^{16}$, $OR^{15}$, $SR^{15}$, $SO_3R^{15}$, $OC(O)R^{15}$, CN, SCN, β-diketonate, CO, $BF_4^-$, $PF_6^-$, or a bulky, non-coordinating anion.

$R^1$–$R^{16}$ independently of one another, are hydrogen, $C_1$–$C_{20}$-alkyl, $C_2$–$C_{20}$-alkenyl, $C_6$–$C_{20}$-aryl, alkylaryl having 1 to 10 carbon atoms in the alkyl radical and 6–20 carbon atoms in the aryl radical, or $SiR^{17}_3$, where the organic radicals $R^1$–$R^{16}$ may also be substituted by halogens, and in each case two geminal or vicinal radicals $R^1$–$R^{16}$ may also be linked to form a five- or six-membered ring, $R^{17}$ independently of one another, are hydrogen, $C_1$–$C_{20}$-alkyl, $C_2$–$C_{20}$-alkenyl, $C_6$–$C_{20}$-aryl, alkylaryl having 1 to 10 carbon atoms in the alkyl radical and 6–20 carbon atoms in the aryl radical, and in each case two geminal radicals $R^{17}$ may also be linked to form a five- or six-membered ring, n is 1, 2 or 3, and m is 1, 2 or 3, (B) if desired, one or more activator compounds, and (C) if desired, one or more additional conventional olefin-polymerization catalysts.

We have furthermore found olefin polymers obtainable by the process according to the invention, and fibers, films and moldings which comprise the olefin polymers according to the invention.

In order to make the bonding to the cyclopentadienyl ring rigid, the most direct link to the donor function contains at least one sp- or sp²-hybridized carbon atom, preferably at least one to three sp²-hybridized carbon atoms. The direct link preferably contains an unsaturated double bond or an aromatic ring or forms with the donor a partially unsaturated or aromatic heterocyclic system.

The cyclopentadienyl ring is 5 bonded to the metal center, preferably chromium, in the complexes according to the invention and can also be a heterocyclopentadienyl ligand, i.e. the at least one carbon atom may also be replaced by a heteroatom from Group 15 or 16. In this case, a $C_5$ ring carbon atom is preferably replaced by phosphorus. In particular, the cyclopentadienyl ring is substituted by further alkyl groups, which can also form a five- or six-membered ring, for example tetrahydroindenyl, indenyl, benzindenyl or fluorenyl.

The donor is a neutral functional group containing an element from the 15th or 16th group of the Periodic Table of the Elements, for example amine, imine, carboxamide, carboxylate, ketone (oxo), ether, thioketone, phosphine, phosphite, phosphine oxide, sulfonyl or sulfonamide, or an unsubstituted, substituted or fused, partially unsaturated heterocyclic or heteroaromatic ring system.

Preference is given to substituted monocyclopentadienyl, monoindenyl, monofluorenyl and heterocyclopentadienyl complexes of the formula I $$[Y-M-X_n]_m \qquad I,$$

where:

M is chromium, molybdenum or tungsten

Y is described by the formula II

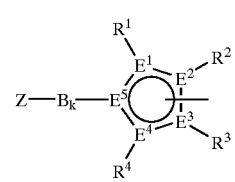

II where:

$E^1$–$E^5$ are carbon or a maximum of one $E^1$ to $E^5$ is phosphorus or nitrogen, Z is $NR^5R^6$, $PR^5R^6$, $OR^5$, $SR^5$ or an unsubstituted, substituted or fused, partially unsaturated heterocyclic or heteroaromatic ring system, B is one of the following groups:

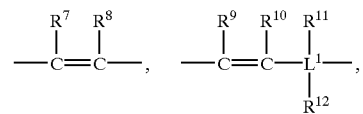

and in addition, if Z is an unsubstituted, substituted or fused, partially unsaturated heterocyclic or heteroaromatic ring system, may alternatively be

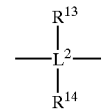

where $L^1$ and $L^2$ are silicon or carbon, k is 1, and is alternatively 0 if Z is an unsubstituted, substituted or fused, partially unsaturated heterocyclic or heteroaromatic ring system, X independently of one another, are fluorine, chlorine, bromine, iodine, hydrogen, $C_1$–$C_{10}$-alkyl, $C_2$–$C_{10}$-alkenyl, $C_6$–$C_{20}$-aryl, alkylaryl having 1–10 carbon atoms in the alkyl radical and 6–20 carbon atoms in the aryl radical, $NR^{15}R^{16}$, $OR^{15}$, $SR^{15}$, $SO_3R^{15}$, $OC(O)R^{15}$, CN, SCN, β-diketonate, CO, $BF_4^-$, $PF_6^-$, or bulky, non-coordinating anions, $R^1$–$R^{16}$ independently of one another, are hydrogen, $C_1$–$C_{20}$-alkyl, $C_2$–$C_{20}$-alkenyl, $C_6$–$C_{20}$-aryl, alkylaryl having 1 to 10 carbon atoms in the alkyl radical and 6–20 carbon atoms in the aryl radical, or $SiR^{17}_3$, where the organic radicals $R^1$–$R^{16}$ may also be substituted by halogens, and in each case two geminal or vicinal radicals $R^1$–$R^{16}$ may also be linked to form a five- or six-membered ring, $R^{17}$ independently of one another, are hydrogen, $C_1$–$C_{20}$-alkyl, $C_2$–$C_{20}$-alkenyl, $C_6$–$C_{20}$-aryl, alkylaryl having 1 to 10 carbon atoms in the alkyl radical and 6–20 carbon atoms in the aryl radical, and in each case two geminal radicals $R^{17}$ may also be linked to form a five- or six-membered ring, n is 1, 2 or 3, and m is 1, 2 or 3.

A particularly suitable transition metal M is chromium.

Y is a substituted cyclopentadienyl system, where the radical —$B_K$—Z carries a rigidly bonded donor function. The cyclopentadienyl ring is bonded to the transition metal via an η⁵-bond. The donor can be bonded coordinatively or non-coordinatively. The donor is preferably coordinated intramolecularly to the metal center.

$E^1$ to $E^5$ are preferably four carbon atoms and one phosphorus atom or only carbon atoms, and very particularly preferably all of $E^1$ to $E^5$ are carbon.

Z can, for example, form an amine, ether, thioether or phosphine together with the bridge B. However, Z can also be an unsubstituted, substituted or fused, heterocyclic aromatic ring system, which, besides carbon ring members, may also contain heteroatoms from the group consisting of oxygen, sulfur, nitrogen and phosphorus. Examples of 5-membered heteroaryl ring groups, which, besides carbon atoms, may also contain one to four nitrogen atoms or one to three nitrogen atoms and/or one sulfur or oxygen atom as ring members, are 2-furyl, 2-thienyl, 2-pyrrolyl, 3-isoxazolyl, 5-isoxazolyl, 3-isothiazolyl, 5-isothiazolyl, 1-pyrazolyl, 3-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 5-imidazolyl, 1,2,4-oxadiazol-3-yl, 1,2,4-oxadiazol-5-yl, 1,3,4-oxadiazol-2-yl or 1,2,4-triazol-3-yl. Examples of 6-membered heteroaryl groups, which may contain one to four nitrogen atoms and/or one phosphorus atom, are 2-pyridinyl, 2-phosphabenzolyl, 3-pyridazinyl, 2-pyrimidinyl, 4-pyrimidinyl, 2-pyrazinyl, 1,3,5-triazin-2-yl and 1,2,4-triazin-3-yl. 1,2,4-triazin-5-yl or 1,2,4-triazin-6-yl. The 5- and 6-membered heteroaryl ring groups here may also be substituted by $C_1$–$C_{10}$-alkyl, $C_6$–$C_{10}$-aryl, alkylaryl having 1 to 10 carbon atoms in the alkyl radical and 6–10 carbon atoms in the aryl radical, trialkylsilyl or halogens, such as fluorine, chlorine or bromine, or may be fused to one or more aromatic or heteroaromatic ring systems. Examples of benzo-fused 5-membered heteroaryl groups are 2-indolyl, 7-indolyl, 2-cumaronyl, 7-cumaronyl, 2-thionaphthenyl, 7-thionaphthenyl, 3-indazolyl, 7-indazolyl, 2-benzimidazolyl and 7-benzimidazolyl- Examples of benzo-fused 6-membered heteroaryl groups are 2-quinolyl, 8-quinolyl, 3-cinnolyl, 8-cinnolyl, 1-phthalazyl, 2-quinazolyl, 4-quinazolyl, 8-quinazolyl, 5-quinoxalyl, 4-acridyl, 1-phenanthridyl and 1-phenazyl. The naming and numbering of the heterocyclic systems has been taken from L. Fieser and M. Fieser, Lehrbuch der organischen Chemie [Textbook of Organic Chemistry], 3rd revised edition, Verlag Chemie, Weinheim 1957. In a preferred embodiment, Z is an unsubstituted, substituted or fused, heteroaromatic ring system or $NR^5R^6$. Preference is given here to simple systems which are readily accessible and inexpensive and are selected from the following group:

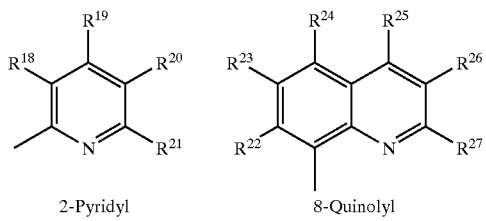

2-Pyridyl          8-Quinolyl

A suitable choice of the radicals $R^{18}$ to $R^{27}$ allows the activity of the catalyst and the molecular weight of the resultant polymer to be influenced. Suitable substituents $R^{18}$ to $R^{27}$ are the same radicals as described for $R^1$–$R^{16}$ and halogens, for example fluorine, chlorine or bromine, where, if desired, it is also possible for two vicinal radicals $R^{18}$ to $R^{27}$ to be linked to form a 5- or 6-membered ring and also to be substituted by halogens, such as fluorine, chlorine or bromine. Preferred radicals RIB to $R^{27}$ are hydrogen, methyl, ethyl, n-propyl, n-butyl, tert-butyl, n-pentyl, n-hexyl, n-heptyl, n-octyl, vinyl, allyl, benzyl, phenyl, naphthyl, biphenyl and anthranyl, and fluorine, chlorine and bromine. Suitable organosilicon substituents are, in particular, trialkylsilyl groups having 1 to 10 carbon atoms in the alkyl radical, in particular trimethylsilyl groups. Z is very particularly preferably an unsubstituted or substituted, for example alkyl-substituted, in particular 8-linked quinolyl, for example 8-quinolyl, 8-(2-methylquinolyl), 8-(2,3,4-trimethyl-quinolyl) or 8-(2,3,4,5,6,7-hexamethylquinolyl). These are very simple to prepare and simultaneously give very good activities.

The rigid bridge B between the cyclopentadienyl ring and the functional group Z is a divalent organic radical consisting of carbon and/or silicon units with a chain length of 1 to 3. The activity of the catalyst can be modified by changing the link length between the cyclopentadienyl ring and the heteroatom donor. Since the nature of Z is also affected by the number of bridging atoms between the cyclopentadienyl radical and the heteroatom, a variety of combinations of B with Z can be chosen here to exert an influence. B can be bonded to Z via $L^1$ or $CR^9$. Owing to the ease of preparation, the combination of B as CH=CH or 1,2-phenylene with Z as $NR^5R^6$ and also of B as $CH_2$, $C(CH_3)_2$ or $Si(CH_3)_2$ and Z as unsubstituted or substituted 8-quinolyl or unsubstituted or substituted 2-pyridyl is preferred. Systems without a bridge B, in which k is 0, are also very particularly simple to prepare. In this case, Z is preferably unsubstituted or substituted quinolyl, in particular 8-quinolyl.

Various properties of the catalyst system can also be modified by varying the substituents $R^1$–$R^{15}$. The accessibility of the metal atom M to the olefins to be polymerized can be modified through the number and type of the substituents, in particular of $R^1$–$R^4$. Thus, it is possible to modify the activity and selectivity of the catalyst with respect to various monomers, in particular sterically hindered monomers. Since the substituents can also affect the rate of termination reactions of the growing polymer chain, this is also a way of modifying the molecular weight of the resultant polymers. The chemical structure of the substituents $R^1$ to $R^{16}$ can therefore be varied within broad ranges in order to achieve the desired results and to obtain a customized catalyst system. Examples of suitable C-organic substituents $R^1$–$R^{16}$ are the following: $C_1$–$C_{20}$-alkyl, where the alkyl may be linear or branched, for example methyl, ethyl, n-propyl, isopropyl, n-butyl, isobutyl, tert-butyl, n-pentyl, n-hexyl, n-heptyl, n-octyl, n-nonyl, n-decyl and n-dodecyl, 5- to 7-membered cycloalkyl, which may itself carry a $C_6$–$C_{10}$-aryl group as substituent, for example cyclopropane, cyclobutane, cyclopentane, cyclohexane, cycloheptane, cyclooctane, cyclononane and cyclododecane, $C_2$–$C_{20}$-alkenyl, where the alkenyl may be linear, cyclic or branched and the double bond may be internal or terminal, for example vinyl, 1-allyl, 2-allyl, 3-allyl, butenyl, pentenyl, hexenyl, cyclopentenyl, cyclohexenyl, cyclooctenyl and cyclooctadienyl, $C_6$–$C_{20}$-aryl, where the aryl radical may be substituted by further alkyl groups, for example phenyl, naphthyl, biphenylyl, anthranyl, o-, m-, p-methylphenyl, 2,3-, 2,4-, 2,5- or 2,6-dimethylphenyl, 2,3,4-, 2,3,5-, 2,3,6-, 2,4,5-, 2,4,6- and 3,4,5-trimethylphenyl, and arylalkyl, where the arylalkyl may be substituted by further alkyl groups, for example benzyl, o-, m- and p-methylbenzyl, 1- and 2-ethylphenyl, where, if desired, two of $R^1$ to $R^{16}$ may also be linked to form a 5- or 6-membered ring, and the organic radicals $R^1$–$R^{16}$ may also be substituted by halogens, for example fluorine, chlorine or bromine. In organosilicon substituents $SiR^{17}_3$, suitable radicals for $R^{17}$ are the same ones as listed in detail above for $R^1$–$R^{16}$, where, if desired, it is also possible for two $R^{17}$ radicals to be linked to form a 5- or 6-membered ring, for example trimethylsilyl, triethylsilyl, butyldimethylsilyl, tributylsilyl, triallylsilyl, triphenylsilyl and dimethylphenylsilyl. Preferred radicals $R^5$–$R^{16}$ are hydrogen, methyl, ethyl, n-propyl, isopropyl, n-butyl, isobutyl, tert-butyl, n-pentyl, n-hexyl, n-heptyl, n-octyl, vinyl, allyl, benzyl, phenyl, orthodialkyl- and-dichlorosubstituted phenyls, trialkyl- and trichloro-substituted phenyls, naphthyl, biphenyl and anthranyl. Particularly suitable organosilicon substituents are trialkylsilyl groups having 1 to 10 carbon atoms in the alkyl radical, in particular trimethylsilyl groups. Particularly preferred radicals $R^5$ and $R^6$ are methyl, ethyl, n-propyl, isopropyl, n-butyl, isobutyl, tert-butyl, n-pentyl, n-hexyl, n-heptyl, n-octyl, allyl, benzyl, phenyl and trialkylsilyl groups. $R^1$ to $R^4$ are preferably hydrogen, methyl, ethyl, n-propyl, isopropyl, n-butyl, isobutyl, tert-butyl, n-pentyl, n-hexyl, n-heptyl, n-octyl, benzyl and phenyl. In preferred transition-metal complexes, $E^1E^2E^3E^4E^5$ together with $R^1R^2R^3R^4$ is a monoalkylcyclopentadienyl radical, for example 3-methylcyclopentadienyl, 3-ethylcyclopentadienyl, 3-isopropylcyclopenta-dienyl or 3-tert-butylcyclopentadienyl, a dialkylcyclopentadienyl radical, for example tetrahydroindenyl, 2,4-dimethylcyclopentadienyl or 3-methyl-5-tert-butylcyclopentadienyl, a trialkyl-cyclopentadienyl radical, for example 2,3,5-trimethylcyclopentadienyl, or a tetraalkylcyclopentadienyl radical, for example 2,3,4,5-tetramethylcyclopentadienyl. Furthermore, preference is also given to compounds in which two vicinal $R^1$ to $R^4$ radicals form a fused six-membered ring system, in which $E^1E^2E^3E^4E^5$ together with $R^1R^2R^3R^4$ is unsubstituted or substituted indenyl, for example indenyl, 2-methylindenyl, 2-ethylindenyl, 2-isopropylindenyl, 3-methylindenyl, 4-phenylindenyl, 2-methyl-4-phenylindenyl or 4-naphthylindenyl, or a benzindenyl system, for example benzindenyl or 2-methylbenzindenyl. In very particularly preferred transition-metal complexes, $E^1E^2E^3E^4E^5$ together with $R^1R^2R^3R^4$ is indenyl.

As in the metallocenes, the transition-metal complexes may be chiral. Thus, on the one hand, the cyclopentadienyl radical can have one or more centers of chirality, or alternatively the cyclopentadienyl system may itself only be enantiotropic, so that the chirality is only induced by bonding thereof to the transition metal M. This can be effected, for example, simply through two different substituents (the donor substituent and, for example, an alkyl radical) on the cyclopentadienyl ring in order to give R- and S-enantiomers of the transition-metal complexes (for the formalism of chirality in cyclopentadienyl compounds, see R. Halterman, Chem. Rev. 92, (1992), 965–994).

The substituents X arise, for example, through the choice of the corresponding metal starting compounds used for the synthesis of the metal complexes, but can also be varied subsequently. Particularly suitable substituents X are the halogens, such as fluorine, chlorine, bromine and iodine, especially chlorine. Simple alkyl radicals, such as methyl, ethyl, propyl, butyl, vinyl, allyl, phenyl and benzyl, also represent advantageous ligands X. Further ligands X which may be mentioned, merely by way of example and in no way to be taken as limiting, are trifluoroacetate, $BF_4^-$, $PF_6^-$ and weakly or non-coordinating anions (see, for example, S. Strauss in Chem. Rev. 1993, 93, 927–942), such as $B(C_6F_5)_4^-$. The designation of the ligands X as anions does not stipulate the type of bonding to the transition metal M. For example, if X is a non- or weakly coordinating anion, the interaction between the metal M and the ligand X is of a rather more electrostatic nature. The various types of bonding are known to the person skilled in the art.

Amides, alkoxides, sulfonates, carboxylates and β-diketonates are also particularly suitable- By varying the radicals $R^{15}$ and $R^{16}$, it is possible, for example, to finely adjust physical properties, such as solubility. The radicals $R^{15}$ and $R^{16}$ are preferably $C_1$–$C_{10}$-alkyl, such as methyl, ethyl, n-propyl, n-butyl, tert-butyl, n-pentyl, n-hexyl, n-heptyl and n-octyl and vinyl, allyl, benzyl and phenyl. Some of these substituted ligands X are very particularly preferred, since they are obtainable from inexpensive and readily accessible starting materials. Thus, a particularly preferred embodiment is for X to be dimethylamide, methoxide, ethoxide, isopropoxide, phenoxide, naphthoxide, triflate, p-toluenesulfonate, acetate or acetylacetonate.

The number n of ligands X depends on the oxidation state of the transition metal M. The number n can thus not be given in general terms. The oxidation state of the transition metals M in catalytically active complexes is usually known to the person skilled in the art. Chromium, molybdenum and tungsten are very probably in the +3 oxidation state. However, it is also possible to employ complexes whose oxidation state does not correspond to that of the active catalyst. Such complexes can then be correspondingly reduced or oxidized by suitable activators. Preference is given to chromium complexes in the +3 oxidation state.

The donor Z can be coordinatively bonded to the transition metal M. This is possible intermolecularly or intramolecularly. The donor Z is preferably coordinatively bonded to M intramomlecularly However, this may change during the polymerization.

The transition-metal complex of the formula I can be in the form of a monomeric, dimeric or trimeric compound, where m is 1, 2 or 3 respectively. It is possible here, for example, for one or more ligands X to bridge two metal centers M.

Preferred complexes are, for example, 1-(8-quinolyl)-2-methyl-4-methylcyclopentadienylchromium(III) dichloride, 1-(8-quinolyl)-3-isopropyl-5-methylcyclopentadienylchromium(III) dichloride, 1-(8-quinolyl)-3-tert-butyl-5-methylcyclopentadienylchromium (III) dichloride, 1-(8-quinolyl)-2,3,4,5-tetramethylcyclopentadienylchromium(III) dichloride, 1-(8-quinolyl)tetrahydroindenylchromium(III) dichloride, 1-(8-quinolyl)indenylchromium(III) dichloride, 1-(8-quinolyl)-2-methylindenylchromium(III) dichloride, 1-(8-quinolyl)-2-isopropylindenylchromium(III) dichloride, 1-(8-quinolyl)-2-ethylindenylchromium(III) dichloride, 1-(8-quinolyl)-2-tert-butylindenylchromium(III) dichloride, 1-(8-quinolyl) benzindenylchromium(III) dichloride, 1-(8-quinolyl)-2-methylbenzindenylchromium(III) dichloride, 1-(8-(2-methylquinolyl))-2-methyl-4-methylcyclopentadienylchromium(III) dichloride, 1-(8-(2-methylquinolyl))-2,3,4,5-tetramethylcyclopentadienylchromium(III) dichloride, 1(8-(2-methylquinolyl))tetrahydroindenylchromium(III) dichloride, 1-(8-(2-methylquinolyl))indenylchromium(III) dichloride, 1-(8-(2-methylquinolyl))-2-methylindenylchromium(III) dichloride, 1-(8-(2-methylquinolyl))-2-isopropylindenylchromium(III) dichloride, 1-(8-(2-methylquinolyl))-2-ethylindenyl chromium(III) dichloride, 1-(8-(2-methylquinolyl))-2-tert-butylindenylchromium(III) dichloride, 1-(8-(2-methylquinolyl))-benzindenylchromium(III) dichloride and 1-(8-(2-methylquinolyl))-2-methylbenzindenylchromium (III) dichloride.

The preparation of functional cyclopentadienyl ligands has been known for some time. Various synthetic routes for these complex ligands are described, for example, by M. Enders et. al. in Chem. Ber. (1996), 129, 459–463 or P. Jutzi and U. Siemeling in J. Orgmet. Chem. (1995), 500, 175–185.

The metal complexes, in particular the chromium complexes, can be obtained in a simple manner if the corresponding metal salts, for example metal chlorides, are reacted with the ligand anion (for example analogously to the examples in DE 19710615).

The olefin polymerization process according to the invention can be combined with all industrially known polymerization processes at temperatures in the range from 20 to 300° C. and under pressures of from 5 to 4000 bar. The advantageous pressure and temperature ranges for carrying out the process are accordingly highly dependent on the polymerization method. Thus, the catalyst systems used in accordance with the invention can be employed in all known polymerization processes, i.e., for example, in high-pressure polymerization processes in tubular reactors or autoclaves, in suspension polymerization processes, in solution polymerization processes or in gas-phase polymerization. In the high-pressure polymerization processes, which are usually carried out at pressures of from 1000 to 4000 bar, in particular from 2000 to 3500 bar, high polymerization temperatures are generally also used. Advantageous temperature ranges for these high-pressure polymerization processes are from 200 to 280° C., in particular from 220 to 270° C. In low-pressure polymerization processes, a temperature which is at least a few degrees below the softening point of the polymer is generally used. In particular, temperatures of from 50 to 180° C., preferably from 70 to 120° C., are used in these polymerization processes. In suspension polymerizations, the polymerization is usually carried out in a suspension medium, preferably in an alkane. The polymerization temperatures are generally in the range from −20 to 115° C., and the pressure is generally in the range from 1 to 100 bar. The solids content of the suspension is generally in the range from 10 to 80%. The polymerization can be carried out batchwise, for example in stirred autoclaves, or continuously, for example in tubular reactors, preferably in loop reactors. In particular, the Phillips-PF process, as described in U.S. Pat. No. 3,242,150 and U.S. Pat. No. 3,248,179, can be used. Of said polymerization processes, gas-phase polymerization, in particular in gas-phase fluidized-bed reactors, solution polymerization, and suspension polymerization, in particular in loop and stirred-tank reactors, are particularly preferred in accordance with the invention. The gas-phase polymerization can also be carried out by the so-called condensed, supercondensed or supercritical method. Different or even the same polymerization processes can also, if desired, be connected in series with one another, forming a polymerization cascade. Furthermore, an additive, for example hydrogen, can be used in the polymerization processes in order to regulate the polymer properties.

The process according to the invention can be used for the polymerization of various olefinically unsaturated compounds, where the term polymerization also includes copolymerization. In contrast to some known iron and cobalt complexes, the transition-metal complexes employed in accordance with the invention have good polymerization activity, even with higher α-olefins, and consequently their suitability for copolymerization should be particularly emphasized. Suitable olefins here, besides ethylene and α-olefins having 3 to 12 carbon atoms, for example propene, 1-butene, 1-pentene, 1-hexene, 1-heptene, 1-octene, 1-nonene, 1-decene and 1-dodecene, are also internal olefins and non-conjugated and conjugated dienes, such as butadiene, 1,5-hexadiene and 1,6-heptadiene, cyclic olefins, such as cyclohexene, cyclopentene and norbornene, and polar monomers, such as acrylates, acrolein, acrylonitrile, vinyl ethers, allyl ethers and vinyl acetate. Vinylaromatic compounds, such as styrene, can also be polymerized by the process according to the invention. Preferably, at least one olefin selected from the group consisting of ethene, propene, 1-butene, 1-pentene, 1-hexene, 1-heptene, 1-octene and 1-decene is polymerized. In a preferred embodiment of the process according to the invention, the monomers used are mixtures of ethylene with $C_3$- to $C_{12}$-α-olefins. In contrast to the situation with some iron and cobalt compounds, higher α-olefins can also be polymerized very well using the catalyst system according to the invention. In a further preferred embodiment of the process according to the invention, an olefin selected from the group consisting of propene, 1-butene, 1-pentene, 1-hexene, 1-heptene and 1-octene is polymerized. These last-mentioned olefins in particular can, in liquefied or liquid state, also form the solvent in the polymerization or copolymerization reaction.

The metal complexes according to the invention in some cases have low polymerization activity, or none at all, and are then brought into contact with an activator, component (B), in order to develop good polymerization activity. Examples of suitable activator compounds are those of the aluminoxane type, in particular methylaluminoxane, MAO. Aluminoxanes are prepared, for example, by the controlled addition of water or water-containing substances to alkylaluminum compounds, in particular trimethylaluminum. Aluminoxane preparations which are suitable as cocatalyst are commercially available. It is assumed that this is a mixture of cyclic and linear compounds. The cyclic aluminoxanes can be summarized by the formula $(R^{28}AlO)_s$ and the linear aluminoxanes by the formula $R^{28}(R^{28}AlO)_sAlR^{28}{}_2$, where s denotes the degree of oligomerization and is a number from about 1 to 50. Advantageous aluminoxanes essentially consist of aluminoxane oligomers having a degree of oligomerization of from about 1 to 30, and $R^{28}$ is preferably a $C_1$–$C_6$-alkyl radical, particularly preferably methyl, ethyl, butyl or isobutyl.

Besides the aluminoxanes, other suitable activator components are those used in so-called cationic activation of metallocene complexes. Activator components of this type are disclosed, for example, in EP-B1-0468537 and EP-B1-0427697. In particular, these activator compounds (B) can be boranes, boroxines or borates, for example trialkylborane, triarylborane, trimethylboroxine, dimethylanilinium tetraarylborate, trityl tetraarylborate, dimethylanilinium boratabenzenes or trityl boratabenzenes (see WO-A-97/36937). Particular preference is given to boranes or borates carrying at least two perfluorinated aryl radicals. Particularly suitable activator compounds (B) are compounds from the group consisting of aluminoxane, dimethylanilinium tetrakispentafluorophenylborate, trityl tetrakispentafluorophenylborate or trispentafluorophenylborane.

It is also possible to employ activator compounds having stronger oxidizing properties, for example silver borates, in particular silver tetrakispentafluorophenylborate, or ferrocenium borates, in particular ferrocenium tetrakispentafluorophenylborate or ferrocenium tetraphenylborate.

The activator component may furthermore be compounds such as alkylaluminum compounds, in particular trimethylaluminum, triethylaluminum, triisobutylaluminum, tributylaluminum, dimethylaluminum chloride, dimethylaluminum fluoride, methylaluminum dichloride, methylaluminum sesquichloride, diethylaluminum chloride and aluminum trifluoride. It is also possible to employ the hydrolysis products of alkylaluminum compounds with alcohols (see, for example, WO-A-95/10546).

The activator compounds may furthermore also be alkyl compounds of lithium, magnesium or zinc, for example methylmagnesium chloride, methylmagnesium bromide, ethylmagnesium chloride, ethylmagnesium bromide, butylmagnesium chloride, dimethylmagnesium, diethylmagnesium, dibutylmagnesium, methyllithium, ethyllithium, methylzinc chloride, dimethylzinc or diethyl zinc.

It is sometimes desirable to use a combination of various activators. This is known, for example, in the case of metallocenes, where boranes, boroxines (WO-A-93/16116) and borates are frequently employed in combination with an alkylaluminum compound. In general, a combination of various activator components with the transition-metal complex according to the invention is also possible.

The amount of activator compounds to be used depends on the type of activator. In general, the molar ratio between the metal complex (A) and the activator compound (B) can be from 1:0.1 to 1:10,000, preferably from 1:1 to 1:2000. The molar ratio between the metal complex (A) and dimethylanilinium tetrakispentafluorophenylborate, trityl tetrakispentafluorophenylborate or trispentafluorophenylborane is from 1:1 to 1:20, preferably from 1:1 to 1:15, particularly preferably from 1:1 to 1:5, and that between the metal complex (A) and methylaluminoxane is preferably from 1:1 to 1:2000, particularly preferably from 1:10 to 1:1000 Since many of the activators, for example alkylaluminum compounds, are simultaneously used to remove catalyst poisons (so-called scavengers), the amount employed depends on the contamination of the other starting materials. However, the person skilled in the art can determine the optimum amount by simple trials.

The transition-metal complex can be brought into contact with the activator compound(s) either before or after contacting with the olefins to be polymerized. Preactivation with one or more activator compounds before mixing with the olefin and further addition of the same or another activator compounds after contacting of this mixture with the olefin is also possible. Preactivation is generally carried out at temperatures of from 10 to 100° C., preferably from 20 to 80° C.

It is also possible for more than one of the transition-metal complexes according to the invention to be brought into contact simultaneously with the olefin to be polymerized. This has the advantage that a further range of polymers can be produced. In this way, bimodal products, for example, can be prepared.

Another broad product range can be achieved by using the complexes according to the invention in combination with at least one conventional olefin-polymerization catalyst (C). Particularly suitable catalysts (C) here are classical Ziegler-Natta catalysts based on titanium, classical Phillips catalysts based on chromium oxides, metallocenes, so-called constrained geometry complexes (see, for example, EP-A-0416815 or EP-A-0420436), nickel and palladium bisimine systems (for their preparation, see WO-A-98/03559), iron and cobalt pyridinebisimine compounds (for their preparation, see WO-A-98/27124) or chromium amides (see, for example, JP-95/170947). Thus, such combinations also allow, for example, the preparation of bimodal products or the in-situ generation of comonomers. In this case, at least one transition-metal complex (A) is preferably used in the presence of at least one conventional olefin-polymerization catalyst (C) and, if desired, one or more activator compounds (B). Depending on the catalyst combinations (A and C), one or more activators are advantageous here. The polymerization catalysts (c) may also be supported and be used simultaneously or in any desired sequence with the complex (A) according to the invention.

The catalysts (A) according to the invention may, if desired, also be immobilized on an organic or inorganic support and used in the polymerization in supported form. This is a common method of avoiding reactor deposits and controlling the polymer morphology. Preferred support materials are silica gel, magnesium chloride, aluminum oxide, mesoporous materials, aluminosilicates and organic polymers, such as polyethylene, polypropylene or polystryene, in particular silica gel or magnesium chloride.

The activator compounds (B) and the metal complex (A) can be brought into contact with the support in various sequences or simultaneously. This is generally carried out in an inert solvent, which can be filtered off or evaporated after the immobilization. However, it is also possible to use the supported catalyst while still moist. Thus, the mixing of the support with the activator compound(s) or the contacting of the support with the polymerization catalyst can be carried out first. Preactivation of the catalyst with one or more activator compounds before mixing with the support is also possible. The amount of metal complex (A) (in mmol) per gram of support material can vary greatly, for example between 0.001 and 1. The preferred amount of metal complex (A) per gram of support material is from 0.001 to 0.5 mmol/g, particularly preferably from 0.005 to 0.1 mmol/g. In a possible embodiment, the metal complex (A) can also be prepared in the presence of the support material. Another type of immobilization is prepolymerization of the catalyst system with or without prior supporting.

The process according to the invention allows the preparation of olefin polymers. The term polymerization, as used here to describe the invention, covers both polymerization and oligomerization, i.e. oligomers and polymers having molecular weights in the range from about 56 to 4,000,000 can be produced by this process.

Owing to their good mechanical properties, the olefin polymers and copolymers prepared using the complexes according to the invention are particularly suitable for the production of films, fibers and moldings. This applies both to the polymers and copolymers obtained using one or more of the substituted monocyclopentadienyl, monoindenyl, monofluorenyl or heterocyclopentadienyl complexes of chromium, molybdenum or tungsten according to the invention and to the combinations thereof with one or more of the conventional olefin-polymerization catalysts (C).

The catalysts according to the invention have very good productivities. If the results from DE-A-19710615 are compared, better (pressure-averaged) activities are found, in particular under industrially relevant polymerization conditions (polymerization time of one hour).

Unexpectedly, the complexes according to the invention are also distinguished by good thermal stability. For example, they can be refluxed for a period of several hours in toluene without decomposing.

The examples below illustrate the invention:

All work was, unless stated otherwise, carried out in the absence of air and moisture. Toluene and THF were dried and distilled over a molecular-sieve column or sodium/benzophenone. Triisobutylaluminum (2 M in heptane) was obtained from Witco, MAO (methylaluminoxane 10% in toluene) and N,N'-dimethylanilinium tetrakis (pentafluorophenyl)borate from Albemarle, and MAO (methylaluminoxane 30% in toluene) from Witco GmbH.

The starting compounds shown below were prepared by the literature methods cited:

8-Bromoquinoline
  a) J. Mirek, Roczniki Chem. 1960, 34, 1599–1606;
  b) E. Reimann in Houben-Weyl, Methoden der Organischen Chemie, 4th Edn., Volume E7a, 366

8-Bromo-2-methylquinoline: C. M. Leir, J. Org. Chem. 1977, 42, 911–913

2,3,4,5-Tetramethylcyclopent-2-enone: F. X. Kohl, P. Jutzi, J. Organomet. Chem. 1983, 243, 119–121

2,3-Dimethylcyclopent-2-enone
  a) M. Dorsch, V, Jäger, W. Sponlein, Angew. Chem. 1984, 96, 815–16; Angew. Chem., Int. Ed. Engl. 1984, 23, 798;
  b) M. Dorsch, Dissertation, University of Wrzburg, 1985

1-(8-Quinolyl)-2,3,4,5-tetramethylcyclopentadiene and 1-(8-quinolyl)-(2,3,4,5-tetramethyl) trimethylsilylcyclopentadiene: M. Enders, R. Rudolph, H. Pritzkow Chem. Ber. (1996), 129, 459–463.

Analysis

NMR samples were taken under an inert gas and sealed in if necessary. The internal standard used in the $^1$H- and $^{13}$C-NMR spectra were the solvent signals, whose chemical shifts were converted to TMS. NMR measurements were carried out using a Bruker AC 200 and, in particular COSY experiments, on a Bruker AC 300.

Mass spectra were measured on a VG Micromass 7070 H and a Finnigan MAT 8230. High-resolution mass spectra were measured on Jeol UMS-700 and VG ZAB 2F instruments.

Elemental analyses were carried out using a Heraeus CHN—O-Rapid.

The comonomer content of the polymer (% $C_6$), its methyl side-chain content per 1000 carbon atoms in the polymer chain ($CH_3/1000$) and its density were determined by IR spectroscopy.

The $\eta$ value was determined using an automatic Ubbelohde viscometer (Lauda PVS 1) at 130° C. using decalin as solvent (ISO 1628 at 130° C., 0.001 g/ml of decalin).

The molecular weight distributions and the means Mn, Mw and Mw/Mn derived therefrom were determined by high-temperature gel permeation chromatography in accordance with DIN 55672 under the following conditions: solvent: 1,2,4-trichlorobenzene, flow rate: 1 ml/min, temperature: 140° C., calibration with PE standards.

Abbreviations used:

| | |
|---|---|
| Cp | cyclopentadienyl |
| Me | methyl |
| Ph | phenyl |
| cat. | catalyst (the transition-metal complex according to the invention) |
| sup.cat. | supported catalyst |
| T | temperature during the polymerization |
| t | polymerization time |
| p | pressure during the polymerization |
| Mw | weight average molecular weight |
| Mn | number average molecular weight |
| Tm | melting point |
| $\eta$ | Staudinger index (viscosity) |
| Density | polymer density |
| $CH_3/1000$ | number of methyl side chains per 1000 carbon atoms |
| % $C_6$ | comonomer content of the polymer in weight % |

General Synthetic Procedure:

Ligand Synthesis:

An equimolar amount of n-BuLi was added to 8-bromoquinoline or N,N-dimethylaniline, and the mixture was subsequently reacted with tetramethylcyclopentenone or 1-indanone. After hydrolysis and acid-catalyzed elimination of water, the corresponding ligand was isolated (yields between 40 and 70%).

Complex Synthesis:

The ligand anions were prepared by deprotonation using n-BuLi or potassium hydride and reacted with the corresponding metal halide. Purification was carried out by reprecipitation or recrystallization (yields generally about 60%).

EXAMPLE 1

1.1. Preparation of 1-(2-N,N-dimethylaminophenyl)-2,3,4,5-tetramethylcyclopentadiene 80.0 ml (0.20 mmol) of n-BuLi in hexane (2.5 M) were slowly added dropwise at 0° C. to 30.0 g (0.25 mol) of N,N-dimethylaniline. The mixture was then refluxed for 52 hours. When the orange solution had cooled to room temperature, 27.6 g (0.20 mol) of tetramethylcyclopentenone were added slowly, and the mixture was refluxed for a further 48 hours. After cooling to room temperature, the orange suspension was poured onto ice and adjusted to pH 2 using conc. hydrochloric acid. The red solution was stirred for a further 30 minutes and rendered alkaline using conc. ammonia solution. The organic phase was separated from the aqueous phase, and the latter was extracted with diethyl ether. The combined organic phases were dried, and the solvent was stripped off under reduced pressure. The crude product was distilled under reduced pressure over a 10 cm Vigreux column at 110–115° C./$10^{-2}$ mbar, giving 14.2 g of 1-(2-N,N-dimethylaminophenyl)-2,3,4,5-tetramethylcyclopentadiene (30%) as an orange oil.

1.2. Preparation of 1-(2-N,N-dimethylaminophenyl)-2,3,4,5-tetramethylcyclopentadienylchromium(III) dichloride A solution of 1.66 mmol of 1-(2-N,N-dimethylaminophenyl)-2,3,4,5-tetramethylcyclopentadienyllithium in 20 ml of THF (from 0.4 g of the corresponding cyclopentadiene compound (1.66 mmol) and 0.66 ml of 2.5 M BuLi in hexane (1.66 mmol)) was slowly added dropwise at room temperature through a septum stopper to a suspension of 0.6 g of $CrCl_3(THF)_3$ (1.66 mmol) in 50 ml of THF using a transfer cannula. The reaction mixture was stirred for 12 hours, and all the volatile constituents were subsequently removed from the blue-green suspension under a high vacuum. The solid which remained was taken up in toluene and filtered. After repeated extraction of the frit residue with hot toluene, the solvent was removed from the combined extracts. The blue-green powder obtained was washed with hexane and dried in a high vacuum. Crystals of the product were obtained from a toluene solution at −30° C. 0.47 g (79%) of 1-(2-N,N-dimethylaminophenyl)-2,3,4,5-tetramethylcyclopentadienylchromium(III) dichloride was isolated.

MS (EI): m/e (%)=362 (10, $M^+$); 326 (100, $M^+$–HCl); 311 (72, $M^+$–HCl, —$CH_3$); 290 (14, $M^+$–2 HCl); 241 (32, $CpMe_4(PhNMe_2)H^+$); 224 ($CpMe_4(PhNMe_2)^+$—$CH_3$, —H); 209 ($CpMe_4(PhNMe_2)^+$-2$CH_3$, —H); 120 (10, N,N-dimethylaniline$^+$)

EXAMPLE 2

Preparation of bis{[1-(2-N,N-dimethylaminophenyl)-2,3,4,5-tetramethylcyclopentadienyl]dicarbonylchromium(I)

Chromium hexacarbonyl (1.14 g, 5.17 mmol) was suspended in 50 ml of n-decane, and 0.8 g of 1-(2-N,N-dimethylaminophenyl)-2,3,4,5-tetramethylcyclopentadiene (3.45 mmol) was added. Slowly warming to 200° C. and refluxing produced a black-brown suspension.

The n-decane was then removed under reduced pressure ($5 \times 10^{-1}$ mbar, 60° C.), and the residue was taken up in dichloromethane and applied to a column (12 cm, $Al_2O_3$, 5% of $H_2O$). It was eluted with dichloromethane as the only, green fraction. Removal of the solvent under a high vacuum gave 0.52 q of bis{[1-(2-N,N-dimethylaminophenyl)-2,3,4,5-tetramethylcyclopentadienyl]-dicarbonylchromium(I)} (22%).

$^1$H-NMR: (200 MHz, $CD_2Cl_2$) $\delta$=1.64, 1.88 (s, 24 H, Cp—$CH_3$); 2.26 (s, 12 H, N—$CH_3$); 6.88 (d, 2 H, CHAr); 7.00 (t, 2 H, CHAr); 7.15–7.21 (m, 2 H, CHAr); 7.53 (d, 2 H, CHAr).

$^{13}$C-NMR: (50 MHz, $CD_2Cl_2$) $\delta$=9.74, 10.22 (Cp-$CH_3$); 29.69, 101.07 (Cp, q); 42.68 (N—$CH_3$); 124.8, 101.3 (CAr, q); 117.6, 120.8, 128.15, 135.98 (CAr, t).

MS (EI): m/e (%)=669 (78, $M^+$–CO, +H), 584 (52, $M^+$–4 CO), 290 (100, $M^+$/2–2CO–2H), 241 (20, $CpMe_4(PhMe_2)^+$)

FT—IR: ($CH_2Cl_2$) $\nu$ ($cm^{-1}$)=1849.5 (vs, $\nu_{M—C=O}$), 187.5(m, $\nu_{M—C=O}$)

EXAMPLE 3

Photochemical Preparation of 1-(2-N,N-dimethylaminophenyl)-2,3,4,5-tetramethylcyclopentadienylchromium(III) dichloride A solution of 0.15 g of bis{[1-(2-N,N-dimethylaminophenyl)-2,3,4,5- tetramethylcyclopentadienyl) dicarbonylchromium(I)} (0.21 mmol) in 50 ml of dichloromethane was irradiated for 48 hours with a mercury high-pressure lamp. A color change of the initially green solution to blue was observed. When the irradiation was complete, the reaction mixture was evaporated under reduced pressure and covered with a layer of hexane at room temperature. Blue needles crystallized from the hexane layer. EI mass spectroscopic analysis of these showed that they were the complex 1-(2-N,N-dimethylaminophenyl)-2,3,4,5-tetramethylcyclopentadienylchromium(III) dichloride (0.05 g, 32%).

EXAMPLE 4

Preparation of 1-[2-(N,N-dimethylaminophenyl)] indene 36 ml of n-BuLi (2.5 M in hexane, 0–09 mmol) were added dropwise with stirring at room temperature to 18 g of N,N-dimethylaniline (0.14 mmol). When the addition was complete, the mixture was refluxed at 100° C. for 72 hours, giving a yellow suspension, to which 11.8 g of 1-indanone (0.09 mmol) in 30 ml of THF were added dropwise with ice-cooling. The mixture was then refluxed for a further three hours and cooled to room temperature, ice and then hydrochloric acid were added to pH 1, and the mixture was stirred for 30 minutes, neutralized using ammonia solution and stirred for a futher half an hour. The phases were separated, the aqueous phase was extracted with diethyl ether, and the combined organic phases were dried, filtered and evaporated to dryness under reduced pressure. The crude product obtained was the hydroxyl compound, which was again treated with hydrochloric acid to pH=0, refluxed for 2 hours and subsequently neutralized and distilled at 125° C./7×10$^{-2}$ mbar, giving 3.1 g of 1-[2-(N,N-dimethylaminophenyl)]indene (14%) as a brown oil.

MS (EI): m/e (%)=235 (M$^+$, 100.0), 220 (M$^+$–CH$_3$, 52)

EXAMPLE 5

Synthesis of 1-(8-quinolyl)-2,3-dimethylcyclopentadiene 5 ml of n-BuLi (2.5 M in hexane, 12.5 mmol) were added dropwise at −95° C. to a solution of 2.5 g of 8-bromoquinoline (12 mmol) in 120 ml of THF, the mixture was stirred for 15 minutes, and 1.3 g of 2,3-dimethylcyclopent-2-enone (12 mmol) dissolved in 10 ml of THF were subsequently added. After warming to room temperature, the solution was refluxed for one hour. The cooled reaction mixture was hydrolyzed using ice, acidified using hydrochloric acid and then neutralized using ammonia solution. The aqueous phase was extracted with diethyl ether, and the combined organic phases were dried. Distillation at 150° C./0.05 mbar gave 1.1 g of 1-(8-quinolyl)-2,3-dimethylcyclopentadiene (40%) as a yellow, viscous oil.

$^1$H-NMR: (200 MHz, CDCl$_3$) δ=1.90 (s, 3H, CH$_3$); 2.03 (s, 3H, CH$_3$); 3.59 (m, 2H, CH$_2$); 6.19 (s, 1H, CH); 7.32–7.73 (m, 4H, quinoline-H); 8.13 (dd, 1H); 8.89 (dd, 1H)

$^{13}$C-NMR: (50 MHz, CDCl$_3$) δ=12.4, 14.1 (CH$_3$); 44.4 (CH$_2$); 120.5, 125.8, 126.3, 127.1, 129.8, 135.9, 149.4 (CH); 128.5, 135.9, 139.1, 140.0, 143.8. 146.8 (quat. C).

MS (EI): m/e (%)=221 (86) [M$^+$]; 220 (100) [M$^+$—H]; 206 (31) [M$^+$–CH$_3$]; 191 (9) [M$^+$–2CH$_3$]

EXAMPLE 6

Preparation of 1-(8-quinolyl)-2,3,4,5-tetramethylcyclopentadienylchromium(III) dichloride from 1-(8-quinolyl)-2,3,4,5-tetramethylcyclopentadienylpotassium 0.4 g of 1-(8-quinolyl)-2,3,4,5-tetramethylcyclopentadiene (1.61 mmol) was added with stirring to 0.06 g of potassium hydride 1.61 mmol) in 20 ml of THF. After the mixture had been stirred for three hours, a red solid precipitated from the solution. This suspension was transferred, by means of a transfer cannula, into a mixture of 0.6 g of CrCl$_3$(THF)$_3$ in 20 ml of THF at room temperature. After the mixture had been stirred for 16 hours, the THF was removed under a high vacuum, and the solid was taken up in toluene. The insoluble potassium chloride was separated off. The solvent was removed, and the residue was washed with hexane and dried under a high vacuum. 0.4 q of green powder was isolated as product in a yield of 70%.

MS (EI): m/e (%)=370 (12, M$^+$); 334 (19, M$^+$–Cl); 249 (99, Me$_4$C$_5$ (quinoline)$^+$—H)

HR-EI-MS:370.02213 (calc.), 370.02203 (measured).

EXAMPLE 7

Preparation of 1-(8-quinolyl)-2,3,4,5-tetramethylcyclopentadienylchromium(III) dichloride from 1-(8-quinolyl)-2,3,4,5-tetramethyltrimethylsilylcyclopentadiene 0.08 g of CrCl3 (THF)$_3$ (0.23 mmol) was suspended in 20 ml of toluene, and 0.08 g of 1-(8-quinolyl)-2,3,4,5-tetramethyltrimethylsilylcyclopentadiene (0.23 mmol) was added. The reaction mixture was refluxed for three hours and stirred for a further 16 hours at room temperature, and the toluene was then distilled off under a high vacuum. The green powder obtained was washed with hexane and dried under a high vacuum.

MS (EI): m/e (%)=370 (12, M$^+$); 334 (19, M$^+$–Cl); 249 (99, Me$_4$Cp (quinoline)$^+$—H)

EXAMPLE 8

1-(8-quinolyl)indenylchromium(III) dichloride

8.1. Preparation of 1-(8-Quinolyl)Indene

8-Bromoquinoline (10.4 g, 50 mmol) was introduced into 100 ml of THF, and the mixture was cooled to about −100° C. 20 ml of n-BuLi (2.5 M in hexane, 50 mmol) were added dropwise, during which the internal temperature was kept below −80° C. When the addition was complete, the mixture was stirred at −80° C. for a further 15 minutes, and 6.6 g of 1-indanone (50 mmol), dissolved in 30 ml of THF, were then added dropwise. The reaction mixture was then allowed to warm slowly to room temperature, and was then refluxed for 3 hours. After the mixture had cooled to room temperature, firstly ice and then hydrochloric acid were added to about pH 1, and the mixture was stirred for 30 minutes. The aqueous and organic phases were separated, the aqueous phase was treated with ammonia solution to about pH 9 and extractetd with ether, and the combined organic phases were subsequently evaporated to dryness under reduced pressure. The viscous oil obtained in this way (1-(8-quinolyl)-indan-1-ol (8H$_2$O)) was treated with hydrochloric acid to pH 0, refluxed for 2 hours and subsequently neutralized. After work-up and drying, 6.6 g of 1-(8-quinolyl)indene (55%) were isolated as a colorless solid.

1-(8-Quinolyl)-indan-1-ol (8H$_2$O)

$^1$H-NMR: (200 MHz, CDCl$_3$) δ=2.58–2.87 (m, 3H, CH$_2$); 6.94 (dd, 1H, quinoline CH); 7.24–7.36 (m, 4H, CH);

7.44–7.50 (m, 2H, H3, H6); 7.70 (dd, 1H, quinoline CH); 8.23 (dd, 1H); 8.66 (s, br, IR, OH); 8.92 (dd, 1H). $^{13}$C-NMR: (200 MHz, CDCl$_3$) δ=30.2, 44.8 (CH$_2$); 87.2 (COH); 120.8, 124.7, 125.1, 126.4, 126.9, 127.2, 127.5, 128.2, 137.9, 147.7 (CH); 127.4, 129.2, 142.6, 143.8, 146.7 (quat. C).

1-(8-Quinolyl)indene m.p.: 108° C.

$^1$H-NMR: (200 MHz, CDCl$_3$) δ=3.69 (d, 2H, CH$_2$); 6.80 (t, 1H =CH); 7.12–7.26 (m, 3H); 7.41 (dd, 1H); 7.55–7.64 (m, 2H); 7.81–7.88 (m, 2H); 8.21 (dd, 1H); 8.92 (dd, 1H).

$^{13}$C-NMR: (50 MHz, CDCl$_3$) δ=38.8 (CH$_2$); 121. 0, 121.2, 123.8, 124.5, 125.8, 126.3, 127.8, 130.0, 133.5, 136.1, 150.0 (CH); 128.6, 135.9, 143.7, 144.0, 145.6, 146.7 (quat. C).

MS (EI): m/e (%)=243 (65) [M$^+$]; 242 (100) [M$^+$—H].

HR-MS (EI): 243.1048 (calc.), 243.1038 (found).

C,H,N analysis: calc.: 88.86% C; 5.39% H; 5.75% N; found: 87.55% C; 5.52% H; 5.92% N.

8.2. Preparation of 1-(8-quinolyl)indenylchromium (III) dichloride 0.05 g of potassium hydride (1.23 mmol) was suspended in 20 ml of THF, and 0.3 g of 1-(8-quinolyl)indene (1.23 mmol) was slowly added. The resultant violet suspension was stirred at room temperature for three hours and then added dropwise to a mixture of 0.46 g of chromium(III) chloride 3THF (1.23 mmol) in 50 ml of THF and, when the addition was complete, the mixture was stirred for a further 16 hours. The solvent was removed under reduced presssure, and the resultant solid was extracted with hot toluene. After the solvent had been distilled off from the combined extracts, the product was obtained as a green powder, which was washed a number of times with hexane and dried under a high vacuum, giving 0.22 g of 1-(8-quinolyl) indenylchromium(III) dichloride (50%).

Alternatively, the residue was taken up in methylene chloride and, after removal of potassium chloride and the solvent, the chromium complex was likewise obtained.

MS (El): m/e (%)=364 (0.2, M$^+$); 329 (0.1, M$^+$–Cl); 242 (100, ind(quinoline)$^+$)

HR-EI-MS:363.97519 (calc.), 363.97615 (measured)

EXAMPLE 9

9.1. Preparation of 1-(8-quinolyl)-2-methylindene 6.70 ml of n-BuLi (16.8 mmol) were added dropwise at 100° C. to 3.50 g of o-bromoquinoline (16.8 mmol) dissolved in 50 ml of THF, and the mixture was subsequently stirred at 80° C. for 15 minutes. A solution of 50 ml of THF and 2.45 g of 2-methyl-1-indanone (16.8 mmol) was then added to the lithiated bromoquinoline over the course of 10 minutes. The mixture was allowed to cool to room temperature, and the solution was then refluxed for three hours, cooled to room temperature, acidified to pH 1 using ice and hydrochloric acid and subsequently refluxed for three hours. The reaction mixture was adjusted to pH 9 using ammonia solution, and the aqueous phase was extracted with diethyl ether. The combined organic phases were dried, and the solvent was removed. The crude product was purified by distillation under reduced pressure at 150–160° C./10$^{-2}$ mbar, giving 1.5 g of 1-(8-quinolyl)-2-methylindene (45%) as a yellow, viscous resin.

9.2. Preparaiton of 1-(8-quinolyl)-2-methylindenylchromium(III) dichloride 1-(8-quinolyl)-2-methylindene (0.3 g, 1.16 mmol) was added dropwise with ice-cooling to a suspension of 0.04 g of potassium hydride (1.16 mmol) in 10 ml of THF. The mixture was then warmed to room temperature and stirred for three hours. The deep-violet solution was added dropwise at −30° C. to CrCl$_3$ (THF)$_3$ in 20 ml of THF. When the addition was complete, the reaction mixture was warmed, the solvent was removed under reduced pressure, the residue was extracted with warm toluene, and precipitated potassium chloride was filtered off. Removal of the solvent under a high vacuum gave 0.35 g of 1-(8-quinolyl)-2-methylindenylchromium(III) dichloride (79%) as a green powder.

EXAMPLE 10

10.1. Preparation of 1-(2-methyl-8-quinolyl)-2,3,4,5-tetramethylcyclopentadiene A solution of 4.4 g of 8-bromo-2-methylquinoline (20 mmol) in 50 ml of THF was cooled to −78° C., and 8.8 ml of n-BuLi (2.5 M in hexane, 22 mmol) were added dropwise with stirring. After the mixture had been stirred for 10 minutes, 3.5 g of 2,3,4,5-tetramethylcyclopentenone (25 mmol) were added dropwise, and the solution was warmed to room temperature, refluxed for one hour and cooled. Ice and hydrochloric acid were added to about pH 1, the mixture was neutralized using ammonia solution, the phases were separated, and the aqueous phase was extracted with pentane. After the combined organic extracts had been dried, the pentane was removed under reduced pressure, and the brown oil which remained was distilled under a high vacuum (b.p.: 115° C./0.01 mbar). 1-(2-Methyl-8-quinolyl)-2,3,4,5-tetramethylcyclopentadiene was obtained as a yellow, viscous oil in a yield of 60% (3.2 g).

$^1$H-NMR: (200 MHz, CDCl$_3$) δ=6a: 1.55 (s, 6H); 1.78 (s, 6H); 2.64 (s, 3H); 5.53 (s, 1H); 6.84 (dd, 1H); 7.12–7.50 (m, 3H); 7.90 (d, 1H). 6b: 0.71 (d, $^3$J(H,H)=7.6 Hz, 3H); 1.82 (s, 3H); 1.87–1.88 (m, 6H); 2.58 (s, 3H); 4.20 (m, 1H); 7.09–7.55 (m, 4H), 7–89 (d, 1H).

$^{13}$C-NMR: (50 MHz, CDCl$_3$) δ=6a: 11.2, 11.3 (CH$_3$); 25.6 (quinoline CH$_3$); 56.3 (allyl CH); 121.3, 125.7, 126.4, 130.5 , 136.2 (quinoline CH), 135.6, 138.9, 139.0, 1412.8, 147.0, 157.4 (quat. C). 6b: 12.0, 12.2, 13.0, 14.2 (CH$_3$); 25.7 (quinoline CH$_3$); 52.1 (allyl CH); 121.4, 125.0, 125.3, 125.8, 136.0 (quinoline CH); 126–7, 126.8, 131.2, 134.6, 138.4, 142.7, 146.7, 157.8 (quat. C).

MS (EI): m/e (%)=263 (85) [M$^+$]; 262 (100) [M$^+$—H ]; 248 (98) [M$^+$—CH$_3$]; 232 (20) [M$^+$—H ]–2CH$_3$]; 218 (10) [M$^+$–3CH$_3$].

HR-MS (EI):263.1674 (calc.), 263.1647 (found)

10.2. Preparation of 1-(2-methyl-8-quinolyl)-2,3,4,5-tetramethylcyclopentadienylchromium(III) dichloride 0.3 g of 1-(2-methyl-8-quinolyl)-2,3,4,5-tetramethylcyclopentadiene (1.14 mmol) in 30 ml of THF was deprotonated using 0.45 ml of n-butyllithium (2.5 M in hexane, 1.14 mmol). After the mixture had been stirred for two hours, the red solution was added dropwise to a suspension of chromium(III) chloride in 20 ml of THF. After the mixture had been stirred at room temperature for 16 hours, the solvents were evaporated off, and the resultant residue was taken up in 20 ml of toluene. The green suspension was filtered, and the residue was extracted a number of times with hot toluene. Conventional work-up gave the product as a green powder (0.22 g) in a yield of 50%.

MS (EI): m/e (%)=384 (54, M$^+$); 348 (100, M$^+$—Cl); 263 (62, M$^+$-2Cl—Cr+2H); 248 (49, M$^+$-2Cl —Cr—CH).
HR-EI-MS: 384.03778 (calc.), 384.03775 (measured).

EXAMPLES 11 TO 27

Polymerization with Ethene

The polymerization examples listed in Table 1 were carried out at an ethene pressure of 1 bar in a 50 or 250 ml flask with overpressure valve.

The complexes were suspended in the respective amount of toluene and activated using the appropriate amount of methylaluminoxane, after which homogeneous violet solutions formed. A stream of ethene was then passed over the mixture with stirring. The reaction vessel was held at the stated temperature by means of a water bath. When the polymerization was complete, the polymers obtained were stirred for ten minutes with methanol in hydrochloric acid. The polyethylene was obtained as a white solid, which was filtered off, washed with methanol and dried at 90° C.

In Examples 11 to 16, the complex from Example 1 (1-(2-N,N-dimethylaminophenyl)-2,3,4,5-tetramethylcyclopentadienylchromium(III) dichloride) was used, in Examples 17 to 20, the complex from Example 6 (1-(8-quinolyl)-2,3,4,5-tetramethylcyclopentadienylchromium(III) dichloride) was used, and in Examples 21 to 27, the complex from Example 8 (1-(8-quinolyl)indenylchromium(III) dichloride) was used.

EXAMPLES 29 TO 51

Polymerization of Ethene and Copolymerization of Ethene with 1-hexene

The polymerization experiments were carried out in a 1 l four-neck flask fitted with contact thermometer, stirrer with Teflon blade, heating mantle and gas-inlet tube. In each case, from 5 to 20 p$\mu$mol of the complexes were introduced into 250 ml of toluene at 40° C. under argon.

On activation with MAO, in each case the amount stated in Table 2 of 1.6 M MAO in toluene were added.

On activation with borate, the amount of DMAB (dimethylanilinium tetrakis(pentafluorophenyl)borate) stated in Table 2 was added, the mixture was heated to 70° C., and TiBAl (triisobutylaluminium) was then added. The solution was then cooled to 40° C., and a stream of about 20 to 40 l/h of ethylene was then passed in at , atmospheric pressure for one hour. In the copolymerization experiments, 5 ml of hexene were introduced before the addition of ethylene, and a stream of ethylene was then passed in. The remainder of the hexene was metered in via a dropping funnel over the course of 15 minutes.

The reaction was terminated by addition of a mixture of 15 ml of concentrated hydrochloric acid and 50 ml of methanol, and the mixture was stirred for a further 15 minutes, After a further 250 ml of methanol had been added and the mixture had been stirred for 15 minutes, the product was filtered off, washed three times with methanol and dried at 70° C. The polymerization and product data are shown in Table 2.

TABLE 1

Polymerization of ethene

| Ex. | Amount of cat. [mmol]/[mg] | T [° C.] | t [min] | PE [g] | Toluene [ml] | Activity [kg/molCr.h] | Al:Cr | M$_w$ [g/mol] | M$_w$/M$_n$ | T$_m$ [° C.] | η [dl/g] |
|---|---|---|---|---|---|---|---|---|---|---|---|
| 11 | 0.11/40 | 21 | 30 | 2.45 | 30 | 44.5 | 1000:1 | | | 106 | |
| 12 | 0.027/10 | 21 | 20 | 2.08 | 30 | 85.0 | 100:1 | | | 125–129 | |
| 13 | 0.0027/1 | 21 | 30 | 1.82 | 30 | 1398 | 1000:1 | | | | |
| 14 | 0.0054/2 | 21 | 30 | 3.66 | 30 | 1392 | 1000:1 | 0.4 · 10$^5$ | 24.5 | 128 | 0.27 |
| 15 | 0.0054/2 | 21 | 30 | 3.62 | 30 | 1407 | 1000:1 | | | | |
| 16 | 0.0054/2 | 21 | 30 | 10.20 | 200 | 3715 | 1000:1 | | | | |
| 17 | 0.067/25 | 21 | 30 | 0.85 | 30 | 25.4 | 100:1 | | | 125 | |
| 18 | 0.027/10 | 21 | 30 | 5.00 | 30 | 1370 | 1000:1 | | | 122–125 | |
| 19 | 0.0027/1 | 21 | 45 | 4.97 | 30 | 2365 | 1000:1 | | | 126–130 | |
| 20 | 0.0027/1 | 21 | 30 | 1.62 | 30 | 1237 | 1000:1 | | 5.58 | 127 | 1.87 |
| 21 | 0.013/5 | 21 | 10 | 1.35 | 30 | 623 | 100:1 | 115159 | 7.63 | 132 | 2.84 |
| 22 | 0.0054/2 | 21 | 15 | 1.38 | 30 | 1027 | 1000:1 | | | | |
| 23 | 0.0054/2 | 21 | 30 | 10.20 | 200 | 3715 | 1000:1 | 221176 | 47.3 | 125–130 | 3.16 |
| 24 | 0.0054/2 | 120 | 15 | 0.90 | 200 | 666 | 1000:1 | | | | |
| 25 | 0.0054/2 | 120 | 30 | 1.06 | 200 | 314 | 1000:1 | | | | |
| 26[a)] | 0.0054/2 | 120 21 | 15 +15 | 1.70 | 200 | 633 | 1000:1 | | | | |
| 27 | 0.0054/2 | 21 | 30 | 1.79 | 30 | 1325 | 1000:1 | 219141 | 2.17 | 130–135 | 2.16 |

[a)]The polymerization was carried out firstly for 15 minutes at 120° C. and then for 15 minutes at 21° C.

EXAMPLE 28

Copolymerization of Ethene with 1-Hexene Using 1-(8-quinolyl)indenylchromium(III) dichloride as Catalyst The experiment was carried out analogously to Examples 11 to 27 in the presence of 10 ml of 1-hexene. 2 mg (0.0054 mmol) of the chromium complex from Example 8 in 100 ml of toluene were used here. The Al:Cr ratio was 1000:1. The polymerization was terminated after 30 minutes. 3.09 g of copolymer were isolated, corresponding to an activity of 1144 g of polymer/(mmol.bar.h).

In Example 29, the complex from Example 1 (1-(2-N,N-dimethylaminophenyl)-2,3,4,5-tetramethylcyclopentadienyl(III) dichloride was used, in Examples 30 to 34, the complex from Example 6 (1-(8-quinolyl)-2,3, 4,5-tetramethylcyclopentadienyl]-chromium(III) dichloride) was used, in Examples 35 to 45, the complex from Example 8 (1-(8-quinolyl) indenylchromium(III) dichloride) was used, in Examples 46 to 49, the complex from Example 9 (1-(8-quinolyl)-2-methylindenylchromium(III) dichloride) was used, and in Examples 50 to 51, the complex from Example 10 (1-(2-methyl-8-quinolyl)-2,3,4,5-tetramethylcyclopentadienylchromium(III) dichloride) was used.

TABLE 2

Polymerization and product data for Examples 29 to 51

| Ex. | Amount of cat. [mg] (μmol) | MAO [mmol] | Al:Cr | Cr:B | Hexene [ml] | T [° C.] | Activity [kg/mol Crh] | Yield [g] ([min]) | Density [g/cm³] | η [dl/g] | $M_w$ [g/mol] | $M_n$ [g/mol] | $M_w/M_n$ | % $c_6$ | m.p. [° C.] | $CH_3$/ 1000 C |
|---|---|---|---|---|---|---|---|---|---|---|---|---|---|---|---|---|
| 29 | 5.46 (15) | 5.3 | 350 | — | — | 40 | 246 | 3.7 (60') | — | 15.2 | — | — | — | — | — | — |
| 30 | 5.56 (15) | 5.3 | 350 | — | — | 40 | 946 | 14.2 (60') | — | 1.74 | 103001 | 14733 | 6.99 | — | — | — |
| 31 | 7.1 (19) | 6.7 | 350 | — | 30 | 40 | 2620 | 24.9 (30') | 0.919 | 0.88 | 36139 | 10900 | 3.32 | 8.7 | 113.7 | 15.9 |
| 32 | 3.4 (9.1) | — | 80 | 1:1.4 | 20 | 40 | 4560 | 8.3 (12') | 0.914 | 4.05 | 350022 | 120280 | 2.91 | 5.4 | 116.6 | 10.2 |
| 33 | 5.0 (13.5) | 8 | 595 | — | 30 | 40 | 2230 | 30.0 (60') | 0.927 | 0.82 | 21400 | 8824 | 2.43 | 6.7 | 113.7 | 13.6 |
| 34 | 2.1 (5.6) | — | 280 | 1:1.7 | 30 | 40 | 904 | 5.1 (60') | 0.919 | 2.52 | 127045 | 31311 | 4.06 | 4.3 | 117.6 | 8.9 |
| 35 | 5.5 (15) | 5.3 | 350 | — | — | 35 | 107 | 1.6 (60') | — | 22.5 | — | — | — | — | — | — |
| 36 | 6.1 (16.7) | 8.5 | 510 | — | 30 | 60 | 1400 | 23.4 (60') | 0.881 | 2.15 | 132567 | 49540 | 2.68 | 20 | 61.3 | 37.1 |
| 37 | 5.8 (15.8) | 8 | 500 | — | 30 | | 1020 | 16.1 (60') | 0.884 | 6.40 | 740298 | 224534 | 3.3 | 13 | 90.9 | 23.5 |
| 38 | 2.3 (6.3) | 3.15 | 500 | — | 30 | 52 | 873 | 5.5 (60') | 0.904 | 11.6 | — | — | — | 5.9 | 120 | 12- |
| 39 | 1.2 (3.3)ᵃ⁾ | 6.2 | 1870 | — | 30 | 40 | 9700 | 32 (15') | 0.9053 | 11.8 | — | — | — | 6.4 | 99.7 | 12.6 |
| 40 | 1.9 (5.2) | 3.0 | 570 | — | 30 | 40 | 6165 | 16 (30') | 0.9021 | 10.1 | — | — | — | 7.3 | 97.0 | 20.5 |
| 41 | 2 (5.4) | 2.7 | 500 | — | 30 | 40 | 4440 | 12 (30') | 0.9014 | 10.5 | — | — | — | 7.8 | 106.4 | 14.1 |
| 42 | 3.6 (9.8) | 4.9 | 500 | — | — | 40 | 1470 | 7.2 (30') | 0.9042 | 8.92 | — | — | — | 6.0 | 111.6 | 10.0 |
| 43 | 2.5 (6.8) | 3.4 | 500 | — | — | 40 | 4765 | 8.1 (15') | 0.9377 | 10.2 | — | — | — | — | 142.6 | >1 |
| 44 | 1.9 (5.2) | 0.78 | 150 | 1:2.2 | — | 40 | 385 | 2.0 (60') | 0.931 | 26.9 | — | — | — | — | 138.6 | >1 |
| 45 | 2.05 (5.5) | 19.4 | 3520 | — | — | 40 | 2180 | 6.0 (30') | 0.9302 | 9.56 | — | — | — | — | 137.4 | >1 |
| 46 | 2.0 (5.4) | 5.4 | 1000 | — | — | 25 | 1000 | 1.37 (15') | — | 5.78 | — | — | — | — | — | — |
| 47 | 2.0 (5.4) | 5.4 | 1000 | — | — | 25 | 670 | 0.7 (15') | — | 11.75 | — | — | — | — | — | >1 |
| 48 | 2.80 (7.4) | 3.7 | 500 | — | 30 | 40 | 460 | 1.7 (30') | 0.907 | 11.8 | — | — | — | 3.7 | 110.5 | 7.6 |
| 49 | 3.6 (9.5) | 150 | 150 | 1:2 | 30 | 40 | 190 | 0.9 (30') | 0.9027 | 19.4 | — | — | — | 4.0 | 110.4 | 4.9 |
| 50 | 2.0 (5.2) | 5.2 | 1000 | — | — | 25 | 410 | 1.1 (15') | — | 1.13 | — | — | — | — | — | — |
| 51 | 2.1 (5.4) | 5.4 | 1000 | — | — | 25 | 670 | 1.8 (30') | — | 1.21 | — | — | — | — | — | — |

ᵃ⁾The complex was dissolved in 1 ml of 4.8 molar MAO in toluene and diluted with 3 ml of toluene, and then added to the 250 ml of toluene in the autoclave for the polymerization

EXAMPLES 52 TO 56

Autoclave Copolymerizations of Ethylene with 1-hexene

The amounts of MAO (1.6 M in toluene) shown in Table 3, 300 ml of toluene and 50 ml of hexene were introduced into a 1 l steel autoclave. The autoclave was heated to the temperature shown in Table 3, and the catalyst, dissolved in toluene, was metered in with ethylene via a lock, in such a way that the desired ethylene pressure was simultaneously established.

The data on the polymerization conditions and the product properties are shown in Table 3.

In Examples 52 to 54, the complex from Example 6 (1-(8-quinolyl)-2,3,4,5-tetramethylcyclopentadienylchromium(III) dichloride) was used, in Example 55, the complex from Example 1 (1-(2-N,N-dimethylaminophenyl)-2,3,4,5-tetramethylcyclopentadienylchromium(III) dichloride) was used, and in Example 56, the complex from Example 8 (1-(8-quinolyl)indenylchromium(III) dichloride) was used.

TABLE 3

Polymerization and product data for Examples 52 to 56

| Ex. | Amount of cat. [mg] (mol) | MAO [mmol] | Al:Cr | T (p) [° C.] ([bar]) | Productivity [g/g of sup. cat.] | Activity [kg/molCr · h] | Yield [g] ([min]) | Density [g/cm³] | η [dl/cm³] | % $C_6$ | $CH_3$/ 1000 C |
|---|---|---|---|---|---|---|---|---|---|---|---|
| 52 | 1.4* (4) | 0.765 | 190 | 60 (40) | 24290 | 108470 | 34 (5') | 0.9257 | 11.0 | 1.3 | 3.1 |
| 53 | 0.195 (0.5) | 0.765 | 1530 | 70 (20) | 246150 | 1832000 | 48 (3') | 0.9304 | 5.32 | 0.8 | 2.5 |
| 54 | 1.130 (0.35) | 0.765 | 2170 | 70 (10) | 251280 | 336000 | 49 (25') | 0.9294 | 3.02 | 1 | 2.8 |
| 55 | 0.5 (1.37) | 0.765 | 550 | 80 (40) | 74000 | 270070 | 37 (6') | 0.9498 | 1.41 | 1.1 | 2.2 |
| 56 | 1.2 (3.3) | 0.765 | 230 | 70 (20) | 15830 | 115150 | 19 (3') | 0.9195 | 12.05 | ~0.8 | 2.3 |

*The complex was introduced as a powder.

EXAMPLES 57 TO 60

Polymerization of Propene

The corresponding chromium complexes were suspended in 30 ml of toluene, and the appropriate amount of MAO (Table 4) was added in a nitrogen flask. The propene was introduced into the reaction mixture at room temperature via a gas-inlet tube at a gas pressure of 1 bar. After the reaction, the crude product was adjusted to pH 1 using methanol in hydrochloric acid solution. Drying of the organic phase gave the polymers as colorless solids.

In Example 57, the complex from Example 1 (1-(2-N,N-dimethyl-aminophenyl)-2,3,4,5-tetramethylcyclopentadienylchromium(III) dichloride) was used, in Example 58, the complex from Example 6 (1-(8-quinolyl)-2,3,4,5-tetramethylcyclopentadienyl-chromium (III) dichloride) was used, and in Examples 59 and 60, the complex from Example 8 (1-(8-quinolyl)indenylchromium (III) dichloride) was used. The polymerization data are shown in Table 4.

TABLE 4

Polymerization data for Examples 57 to 60

| Ex. | Amount of cat. [mmol]/[mg] | t [min] | Yield [g] | Activity [g PP/mol cat. h bar] | Al:Cr |
|---|---|---|---|---|---|
| 57 | 0.09/33 | 90 | 0.53 | 3.92 | 100:1 |
| 58 | 0.005/2 | 120 | 1.20 | 111 | 100:1 |
| 59 | 0.0054/2 | 240 | 1.06 | 50 | 1000:1 |
| 60 | 0.016/6 | 90 | 0.36 | 15 | 100:1 |

The polypropylene from Example 60 is characterized as follows:

$M_w$: 82024; $M_n$: 7197; $M_w/M_n$: 11.4; viscosity η:0.53.

EXAMPLE 61

Polymerization of 1-hexene

The complex from Example 8 (1-(8-quinolyl) indenylchromium(III) dichloride) (2 mg, 5.4 μmol) was suspended in 10 ml of 1-hexene, and 5.4 mmol of methylaluminoxane (1.6 M in toluene) were added in a 50 ml nitrogen flask, and the mixture was stirred at room temperature for 24 hours. When the polymerization was complete, the reaction mixture was adjusted to pH 1 using methanol in hydrochloric acid solution, and the organic phase was dried under vacuum The complex is capable of polymerizing hexene.

We claim:

1. A substituted monocyclopentadienyl, monoindenyl, monofluorenyl or heterocyclopentadienyl complex of chromium, molybdenum or tungsten in which at least one of the substituents on the cyclopentadienyl ring carries a donor function which is bonded rigidly, not exclusively via sp³-hybridized carbon or silicon atoms, which complex is immobilized on an organic or inorganic support.

2. The immobilized complex defined in claim 1, which is of formula I

[Y—M—X$_n$]$_m$     I, where:

M is chromium, molybdenum or tungsten,

Y is described by formula II

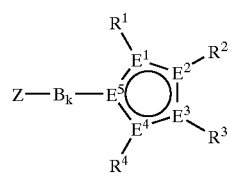

II where:

$E^{1-E5}$ are carbon or a maximum of one $E^1$ to $E^5$ is phosphorus or nitrogen, Z is NR⁵R⁶, PR⁵R⁶, OR⁵, SR⁵ or an unsubstituted, substituted or fused, partially unsaturated heterocyclic or heteroaromatic ring system, B is one of the following groups:

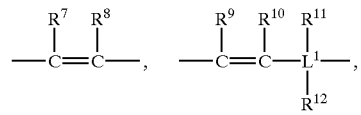

and in addition, if Z is an unsubstituted, substituted or fused, partially unsaturated heterocyclic or heteroaromatic ring system, may alternatively be

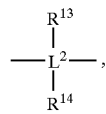

where $L^1$ and $L^2$ are silicon or carbon, k is 1, and is alternatively 0 if Z is an unsubstituted, substituted or fused, partially unsaturated heterocyclic or heteroaromatic ring system, X independently of one another, are fluorine, chlorine, bromine, iodine, hydrogen, $C_1$–$C_{10}$-alkyl, $C_2$–$C_{10}$-alkenyl, $C_6$–$C_{20}$-aryl, alkylaryl having 1–10 carbon atoms in the alkyl radical and 6–20 carbon atoms in the aryl radical, NR¹⁵R¹⁶, OR¹⁵, SR¹⁵, SO₃R¹⁵, OC(O) R¹⁵, CN, SCN, β-diketonate, CO, BF₄⁻, PF₆⁻, or a bulky, non-coordinating anion, $R^1$–$R^{16}$ independently of one another, are hydrogen, $C_1$–$C_{20}$-alkyl, $C_2$–$C_{20}$-alkenyl, $C_6$–$C_{20}$-aryl, alkylaryl having 1 to 10 carbon atoms in the alkyl radical and 6–20 carbon atoms in the aryl radical, or SiR¹⁷₃, where the organic radicals $R^1$–$R^{16}$ may also be substituted by halogens, and in each case two geminal or vicinal radicals $R^1$–$R^{16}$ may also be linked to form a five- or six-membered ring, $R^{17}$ independently of one another, are hydrogen, $C_1$–$C_{20}$-alkyl, $C_2$–$C_{20}$-alkenyl, $C_6$–$C_{20}$-aryl, alkylaryl having 1 to 10 carbon atoms in the alkyl radical and 6–20 carbon atoms in the aryl radical, and in each case two geminal radicals $R^{17}$ may also be linked to form a five- or six-membered ring, n is 1, 2 or 3, and m is 1, 2 or 3.

3. The immobilized complex of chromium defined in claim 1.

4. The immobilized complex defined in claim 2, in which Z is an unsubstituted, substituted or fused, heteroaromatic ring system.

5. The immobilized complex defined in claim 2, in which E¹E²E³E⁴E⁵ together with R¹R²R³R⁴ is unsubstituted or substituted indenyl.

6. The immobilized complex defined in claim 2, in which Z is an unsubstituted or substituted 8-(quinolyl) system, and k is 0.

7. A process for the polymerization or copolymerization of olefins, in which the olefins are polymerized in the presence of the following components:

(A) a substituted monocyclopentadienyl, monoindenyl, monofluorenyl or heterocyclopentadienyl complex of formula I $$[Y-M-X_n]_m \qquad I,$$

where:
M is chromium, molybdenum or tungsten,
Y is described by formula II

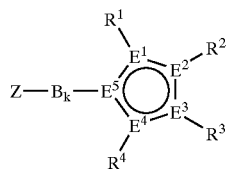

where:
$E^1-E^5$ are carbon or a maximum of one $E^1$ to $E^5$ is phosphorus or nitrogen,
Z is $NR^5R^6$, $PR^5R^6$, $OR^5$, $SR^5$ or an unsubstituted, substituted or fused, partially unsaturated heterocyclic or heteroaromatic ring system,
B is one of the following groups:

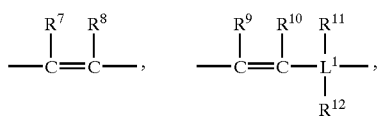

and in addition, if Z is an unsubstituted, substituted or fused, partially unsaturated heterocyclic or heteroaromatic ring system, may alternatively be

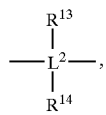

where
$L^1$ and $L^2$ are silicon or carbon,
k is 1, and is alternatively 0 if Z is an unsubstituted, substituted or fused, partially unsaturated heterocyclic or heteroaromatic ring system,
x independently of one another, are fluorine, chlorine, bromine, iodine, hydrogen, $C_1-C_{10}$-alkyl, $C_2-C_{10}$-alkenyl, $C_6-C_{20}$-aryl, alkylaryl having 1–10 carbon atoms in the alkyl radical and 6–20 carbon atoms in the aryl radical, $NR^{15}R^{16}$, $OR^{15}$, $SR^{15}$, $SO_3R^{15}$, $OC(O)R^{15}$, CN, SCN, β-diketonate, CO, $BF_4^-$, $PF_6^-$, or a bulky, non-coordinating anion,
$R^1-R^{16}$ independently of one another, are hydrogen, $C_1-C_{20}$-alkyl, $C_2-C_{20}$-alkenyl, $C_6-C_{20}$-aryl, alkylaryl having 1 to 10 carbon atoms in the alkyl radical and 6–20 carbon atoms in the aryl radical, or $SiR^{17}_3$, where the organic radicals $R^1-R^{16}$ may also be substituted by halogens, and in each case two geminal or vicinal radicals $R^1-R^{16}$ may also be linked to form a five- or six-membered ring,
$R^{17}$ independently of one another, are hydrogen, $C_1-C_{20}$-alkyl, $C_2-C_{20}$-alkenyl, $C_6-C_{20}$-aryl, alkylaryl having 1 to 10 carbon atoms in the alkyl radical and 6–20 carbon atoms in the aryl radical, and in each case two geminal radicals $R^{17}$ may also be linked to form a five- or six-meaibered ring,
n is 1, 2 or 3, and
m is 1, 2 or 3,
(B) optionally one or more activator compounds, and
(C) optionally one or more additional conventional olefin-polymerization catalysts,
wherein the component (A) and/or the component (D) is immobilized on an organic or inorganic support.

8. The process of claim 7, in which at least one olefin selected from the group consisting of ethene, propane, 1-butene, 1-pentene, 1-hexene, 1-heptene, 1-octene and 1-decene is polymerized.

9. The process of claim 7, in which the polymerization is carried out in suspension, in solution or in the gas phase.

10. The immobilized complex of chromium defined in claim 3, wherein the support is selected from the group consisting of silica gel, magnesium chloride, aluminum oxide, mesaporous materials, aluminosilicates, polyethylene, polypropylene and polystyrene.

11. The immobilized complex defined in claim 2, wherein B is $CH_2$, $CH(CH_3)_2$ or $Si(CH_3)_2$, and Z is an unsubstituted or substituted 2-pyridyl or 8-quinolyl radical.

12. The immobilized complex defined in claim 2, wherein M is chromium.

13. The immobilized complex defined in claim 12, wherein Z denotes a group represented by formulae

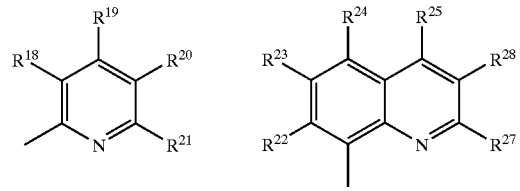

wherein $R^{18}-R^{27}$ independently of one another are hydrogen, $C_1-C_{20}$-alkyl, $C_2-C_{20}$-alkenyl, $C_6-C_{20}$-aryl, alkylaryl having 1 to 10 carbon atoms in the alkyl radical and 6 to 20 carbon atoms in the aryl radical, $SiR^{17}_3$, or halogens, where the organic radicals $R^{18}-R^{27}$ may also be substituted by halogens, and in each case two geminal or vicinal radicals $R^{18}-R^{27}$ may also be linked to form a five- or six-membered ring.

14. The immobilized complex defined in claim 12, wherein the support is selected from the group consisting of silica gel, magnesium chloride, aluminum oxide, mesoporous materials, aluminosilicates, polyethylene, polypropylene and polystyrene.

15. A mixture of components comprising
(A) a substituted monocyclopentadienyl, monoindenyl, monofluorenyl or heterocyclopentadienyl complex of formula I $$[Y-M-X_n]_m \qquad I,$$

where:
M is chromium, molybdenum or tungsten,
Y is described by formula II

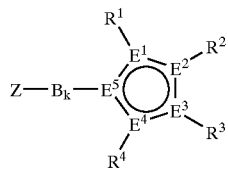

where:
$E^1$–$E^5$ are carbon or a maximum of one $E^1$ to $E^5$ is phosphorus or nitrogen,
Z is $NR^5R^6$, $PR^5R^6$, $OR^5$, $SR^5$ or an unsubstituted, substituted or fused, partially unsaturated heterocyclic or heteroaromatic ring system,
B is one of the following groups:

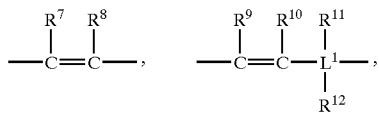

and in addition, if Z is an unsubstituted, substituted or fused, partially unsaturated heterocyclic or heteroaromatic ring system, may alternatively be

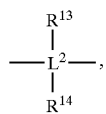

where
$L^1$ and $L^2$ are silicon or carbon,
k is 1, and is alternatively 0 if Z is an unsubstituted, substituted or fused, partially unsaturated heterocyclic or heteroaromatic ring system,
x independently of one another, are fluorine, chlorine, bromine, iodine, hydrogen, $C_1$–$C_{10}$-alkyl, $C_2$–$C_{10}$-alkenyl, $C_6$–$C_{20}$-aryl, alkylaryl having 1–10 carbon atoms in the alkyl radical and 6–20 carbon atoms in the aryl radical, $NR^{15}R^{16}$, $OR^{15}$, $SR^{15}$, $SO_3R^{15}$, $OC(O)R^{15}$, CN, SCN, β-diketonate, CO, $BF_4^-$, $PF_6^-$, or a bulky, non-coordinating anion,
$R^1$–$R^{16}$ independently of one another, are hydrogen, $C_1$–$C_{20}$-alkyl, $C_2$–$C_{20}$-alkenyl, $C_6$–$C_{20}$-aryl, alkylaryl having 1 to 10 carbon atoms in the alkyl radical and 6–20 carbon atoms in the aryl radical, or $SiR^{17}_3$, where the organic radicals $R^1$–$R^{16}$ may also be substituted by halogens, and in each case two geininal or vicinal radicals $R^1$–$R^{16}$ may also be linked to form a five- or six-membered ring,
$R^{17}$ independently of one another, are hydrogen, $C_1$–$C_{20}$-alkyl, $C_2$–$C_{20}$-alkenyl, $C_6$–$C_{20}$-aryl, alkylaryl having 1 to 10 carbon atoms in the alkyl radical and 6–20 carbon atoms in the aryl radical, and in each case two geminal radicals $R^{17}$ may also be linked to form a five- or six-membered ring,
n is 1, 2 or 3, and
m is 1, 2or 3,
(3) optionally one or more activator compounds, and
(C) optionally one or more additional conventional olefin-polymerization catalysts,
wherein component (A) and/or component (B) is immobilized on an organic or inorganic support.

16. The mixture defined in claim 15, wherein the support is selected from the group consisting of silica gel, magnesium chloride, aluminum oxide, mesoporous materials, aluminosilicates, polyethylene, polypropylene and polystyrene.

17. The mixture defined in claim 15, comprising as component (B) a compound selected from the group consisting of aluminoxane, dimethylanilinium tetrakispentafluorophenylborate, trityl tetrakispentafluorophenylborate and trispentafluorophenylborane.

* * * * *